United States Patent [19]

Davis et al.

[11] Patent Number: 5,040,706
[45] Date of Patent: Aug. 20, 1991

[54] LIQUID DROPLET DISPENSING APPARATUS

[75] Inventors: Jeffrey P. Davis, Madison, Wis.; Roy D. Archibald, Fremont, Calif.; Christa D. Nicholas, Alameda, Calif.; Santosh K. Chandrasekaran, Moraga, Calif.

[73] Assignee: InSite Vision, Inc., Alameda, Calif.

[21] Appl. No.: 324,793

[22] Filed: Mar. 17, 1989

[51] Int. Cl.⁵ .................. B65D 17/24; B65D 47/10; A61M 1/00
[52] U.S. Cl. ............................. 222/541; 222/420; 604/295; 604/300
[58] Field of Search ............... 222/420, 541; 604/295, 604/300, 301, 302

[56] References Cited

U.S. PATENT DOCUMENTS

| D. 192,052 | 1/1962 | Akers . | |
|---|---|---|---|
| 897,156 | 8/1908 | Rosenkaimer | 222/420 |
| 1,765,114 | 6/1930 | Turner . | |
| 1,855,653 | 4/1932 | Strauss . | |
| 2,431,192 | 11/1947 | Munson . | |
| 3,178,072 | 4/1965 | Pickels . | |
| 3,300,099 | 1/1967 | Marona . | |
| 3,756,478 | 9/1973 | Podell et al. . | |
| 3,777,949 | 12/1973 | Chiquiari-Arias | 222/541 |
| 4,248,227 | 2/1981 | Thomas | 128/232 |
| 4,338,936 | 7/1982 | Nelson | 604/295 |
| 4,398,909 | 8/1983 | Portnoff | 604/295 |
| 4,471,890 | 9/1984 | Dougherty . | |
| 4,566,613 | 1/1986 | Anscomb | 222/541 |
| 4,787,536 | 11/1988 | Widerström | 222/541 |
| 4,871,091 | 10/1989 | Preziosi | 604/295 |

FOREIGN PATENT DOCUMENTS 3630788  3/1988  Fed. Rep. of Germany ...... 222/210

OTHER PUBLICATIONS

BSS Product Sheet, issued 1986, Alcon Lacrisert Product Sheet, MSD.

Primary Examiner—Andres Kashnikow
Assistant Examiner—Lesley D. Morris
Attorney, Agent, or Firm—Burns, Doane, Swecker & Mathis

[57] ABSTRACT

A disposable unit- or multi-dose liquid dispensing container device, particularly adapted for delivery of ophthalmic liquid medicament in the form of discrete droplets to the eye. The structural configuration of the device including an angularly offset leading end permits the user to employ a free hand for manipulation of the eyelid to enhance reception of the discharge opening of the dispenser into the conjunctival cul-de-sac while at the same time, enabling the user to look directly into a wall-mounted mirror for accurate placement of the medicament. A small capacity reservoir and ease of control of accurate orifice size enables the application of uniform liquid-ejection pressure by the user to deliver droplets of reproducible dosage size with the multi-dose embodiment.

35 Claims, 2 Drawing Sheets

LIQUID DROPLET DISPENSING APPARATUS

FIELD OF THE INVENTION

The present invention relates generally to dispensing devices and pertains, more specifically, to liquid dispensers of the type particularly useful in the dispensing eye drops. The invention is principally directed to a disposable, integrally formed, soft plastic dispenser suitable primarily for self-applied unit-dose or limited-dose dispensing of a liquid medicament to the eye.

BACKGROUND OF THE INVENTION

Dispensing containers for the self-application of liquid medicaments to parts of the body, such as the eye, nose, mouth, etc., are known. Such dispensers are typically of the multi-dosage variety taking the form of a depressible plastic container that contains an amount of the concerned liquid. The amount of liquid contained in such containers permits a multitude of applications thereof over an extended period of time. Such containers normally employ a straight dispensing nozzle which, when used for self-application, requires the user's head to be tilted back and the liquid dispensed from above. Containers of this type are frequently intended for the application of "over-the-counter"-type medicines where critical dosage amounts and danger of contamination need be of only secondary or marginal concern.

Dispensing containers for liquids having the discharge nozzle angularly offset in order to facilitate the self-application of the medicine are known. Such angularly offset nozzles have generally taken the form of reusable nozzles for installation on containers of relatively large, multi-dose capacity. While the angular disposition of the nozzle on such containers permits the liquid to be dispensed from a position other than directly above the eye, or other object part of the body, the size of the container essentially requires the use of both hands for accurately dispensing the liquid, one hand for supporting the container and the other hand for accurately positioning and steadying the nozzle tip. These dispensers, therefore, are of little advantage for the self-insertion of liquid to a part of the body, where it is desirable to hold or otherwise manually prepare the body part for reception of the liquid.

For example, the assignee of the hereindescribed invention has developed a semiviscous eye-drop which is transformed, after administration, to a substantially more viscous, soft, cohesive drug-containing plaque that serves as a "platform" for the sustained release of an active drug. This formulation, which is described in detail in U.S. patent application Ser. No. 301,114, filed Jan. 25, 1989, is preferably administered into the conjunctival cul-de-sac of the eye, rather than onto the cornea in order to avoid a brief stinging sensation and to allow proper plaque formation and retention in a preferred manner. Deliberate placement of the required amount of such liquid in the ocular cul-de-sac can be readily accomplished by a second party, but is difficult to accomplish when self-administration is required.

It is to the amelioration of these problems, therefore, to which the present invention is directed.

SUMMARY OF THE INVENTION

The present invention provides a structurally simple, inexpensive, disposable and hygienically secure liquid dispenser that overcomes the aforementioned problems. The dispensing container of the invention permits self-insertion of a liquid drop into the ocular cul-de-sac by means of a curved or angularly offset delivery nozzle that is integrally formed as part of a small sealed, single- or limited-dose soft plastic container that can be readily operated by simply pinching the container between two fingers, most commonly the thumb and forefinger, of either hand.

The described container with its offset discharge nozzle simplifies self-administration by allowing a person to look directly into a mirror to observe the location and orientation of the delivery device. The curved or angled tip permits safe approach to the eye and deposit of the requisite dosage onto the inner surface of the cul-de-sac. The organization, moreover, facilitates self-administration of the liquid by the ability of the user to position and squeeze the device with one hand while using the other hand to manipulate the lower eye lid in order to expose the inner or conjunctival surface of the cul-de-sac into which the liquid drop is to be placed. Moreover, it will be appreciated that, where self-administration requires two hands and does not permit holding a mirror at a convenient viewing angle, the described drug delivery system permits observation of the insertion of the device in a commonly available wall-mounted mirror, or the like.

The present invention provides, therefore, a liquid dispensing container device comprising a hollow body having an integrally formed reservoir portion and nozzle portion extending therefrom, the reservoir portion including a chamber sized to contain a body of liquid and having compressible walls for expulsion of said liquid from said chamber, and the nozzle portion being offset longitudinally from the body and having a discharge end sealed by a removable closure.

For a better understanding of the invention, its operating advantages and the specific objectives obtained by its use, reference should be made to the accompanying drawings and description which relate to a preferred embodiment thereof.

DETAILED DESCRIPTION OF A PREFERRED EMBODIMENT

Figure 1:
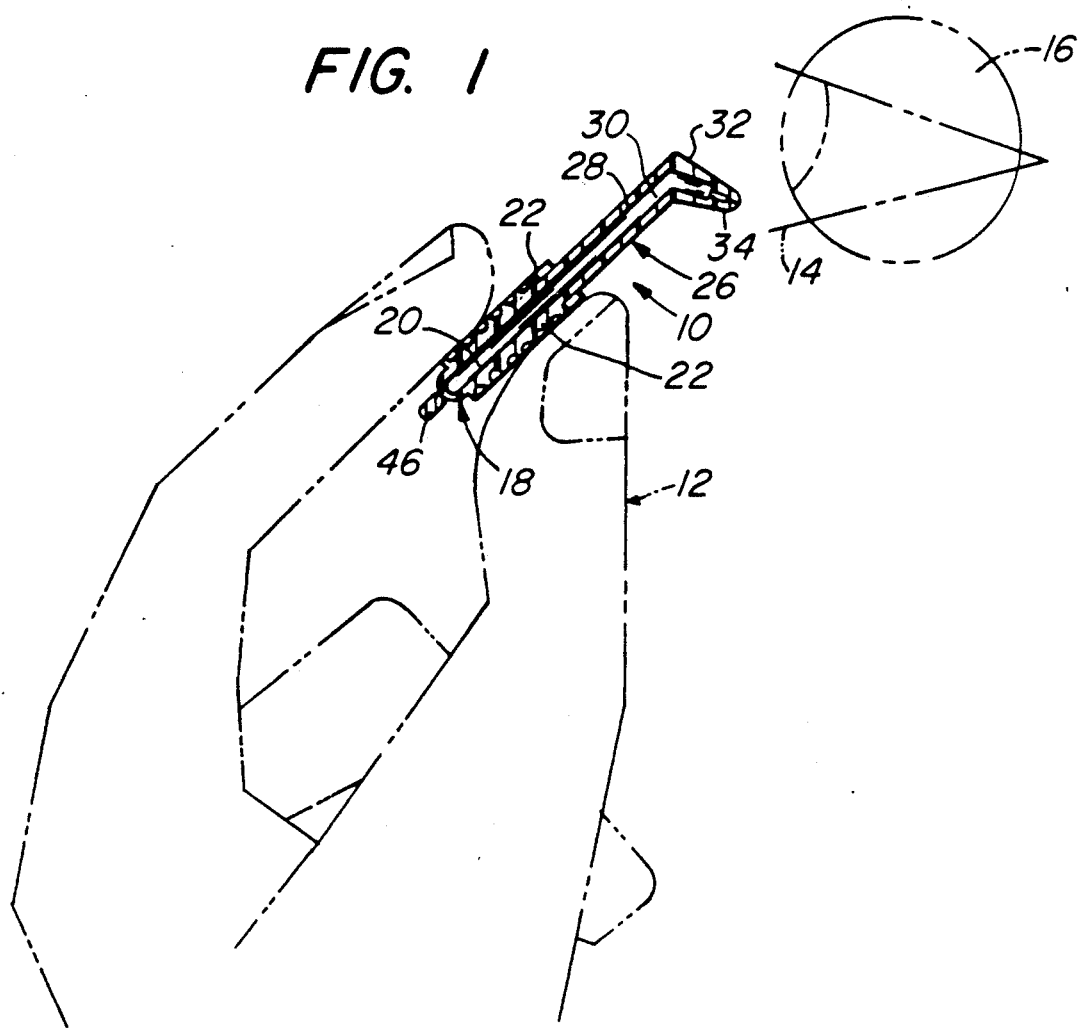
FIG. 1 is a sectional view of the liquid dispensing container device of the invention with a somewhat schematic representation of the hand and eye of the user to illustrate operation of the device.

Referring now to the drawings there is shown a somewhat schematic representation of a liquid dispensing container device 10 operatively held in the hand 11 of a user for dispensing a drop of a contained liquid into the ocular cul-de-sac formed by the extended lower lid 14 of the user's eye 16. The device 10 comprises an elongated hollow body 12 of compressible material, such as low density polyethylene or polypropylene. The body 12 includes at its rear end a reservoir portion 18 whose interior defines a chamber 20 for reception of a body of the liquid to be dispensed. The chamber 20 is bounded on opposite sides by a pair of spaced, flat, generally parallel walls 22 the exterior surface of each of which is knurled or otherwise roughened, as at 24, to assist the user in gripping the device between the thumb and the forefinger as depicted in FIG. 1.

Figure 2:
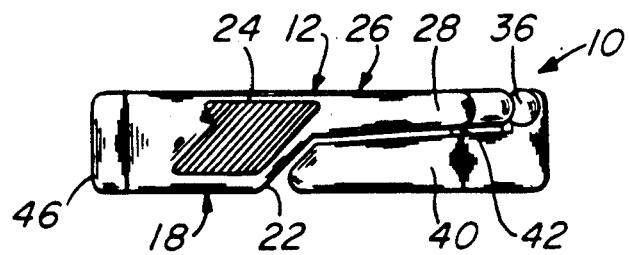
FIG. 2 is a side elevational view of the device shown in FIG. 1.
Figure 4:
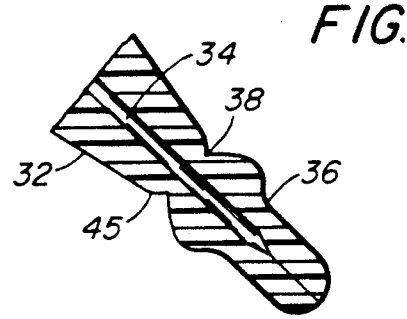
FIG. 4 is an enlarged detailed view of the discharge end of the device.

Extending from the reservoir portion 18 of the body 12 is an integrally formed nozzle portion 26. This portion is defined by a generally cylindrical member 28 that extends from the end of the reservoir portion 18 adjacent one lateral side thereof and that contains a passage 30 communicating at its rear end with the chamber 20. As will be appreciated with reference to FIGS. 2 and, that cylindrical member 28 constitutes a rear end of the nozzle portion 26 which extends from the chamber 20 generally coplanar therewith and in an offset position adjacent one lateral side of the reservoir portion 18. The leading end of the nozzle portion 26 is angularly offset, as at 32, and contains a small diameter discharge passage 34 terminating, prior to use, in a sealing closure 36 (FIG. 4). The diameter of the discharge passage 34 is advantageously sized to produce a liquid drop of predetermined volume upon compression of the walls 22 by the user. The size of the discharge passage is, moreover, such as to permit expression of the drop without requiring excessive effort.

Figure 3:
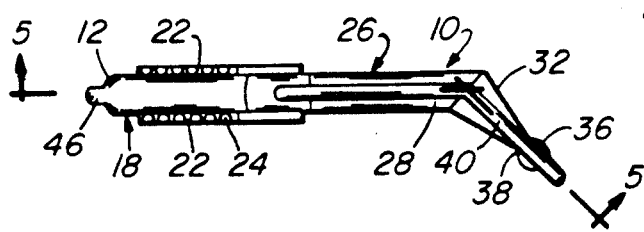
FIG. 3 is a bottom view of the device of FIG. 1.
Figure 5:
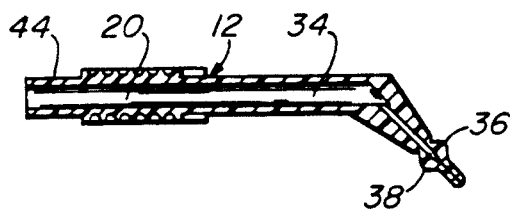
FIG. 5 is a sectional view taken along line 5—5 of FIG. 3.

As will be appreciated with reference to FIGS. 3 and 5, the illustrated angularly offset leading end 32 of the nozzle portion 26 is disposed out of the general plane of the reservoir portion 18 and the rear end of the nozzle portion 26 which is constituted by the cylindrical member 28. The degree of offset of the leading end 32 of the nozzle portion 26 extending to the member 28 may be from about thirty to about sixty degrees with respect to the longitudinal axis of the reservoir portion 18 and of the rear end of the member 28. This angle is determined by the amount of offset required at the tip of the nozzle leading end, taking into consideration the overall size of the device, to permit the user's view of the end installed at the ocular cul-de-sac to be minimally obscured. In practice an angle of about forty-five degrees is preferred.

As best shown in FIG. 4, the end of the passage 34 is sealed by a closure 36 that is integral with the leading end of the nozzle offset. The closure 36 is defined by a bulbous body separated from the nozzle proper by a reduced diameter neck 38 defining a line of weakness that permits the closure to be readily broken from the nozzle to thereby expose the leading end of the discharge passage.

As can best be appreciated from consideration of FIG. 4, in fabricating the device, the closure 36 is molded with a continuous extension of the passage 34. Thereafter, the end is crimped by a heated pressing tool to render the tip liquid impervious, thereby resulting in the configuration shown in FIG. 4.

Advantageously, the device is provided with a support tab 40 that extends between and connects the closure 36 to nozzle portion 26. In this way the connection between the closure 36 and the nozzle portion is protected against inadvertent disruption. As shown, the support tab 40 is a substantially flat body that is connected to the member 28 by longitudinally spaced, frangible webs 42. The tab 40 is configured to substantially complement the space beneath the member 28 and provides sufficient surface area on which to dispose appropriate labelling, or the like.

Figure 6:
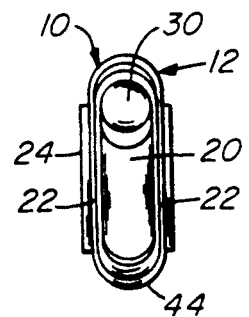
FIG. 6 is an elevational view illustrating the end of the device prior to sealing a body of liquid therein.

With reference to FIGS. 5, and 6, it is apparent that the body 12 is molded with its rear end 44 open for reception of the medicament to be dispensed. While the size of the body 12 and particularly the volume of the chamber 20 may vary to suit the particular medicament of concern, the chamber 20 in the described embodiment is designed to receive about 0.5 ml of sterilized liquid medicament. Following loading of liquid, the end of the body is hermetically sealed, as shown at 46 in FIGS. 1, 3 and 4 by a heated crimping tool (not shown).

The operation of the described dispensing device is as follows. With liquid medicament totally sealed within the device 10, the bulbous closure 36 is broken at the line of weakness defined by the neck 38 to expose the discharge passage 34. It will be noted that, with the closure 36 removed, the free end of the nozzle member 28 is defined by a generally spherically formed surface 45, which helps to protect the user from injury resulting from scratching, or the like, caused by the end of the nozzle.

As shown, in FIG. 1 the user grips the flat walls 22 that define the opposite sides of the reservoir portion 18 with the thumb and forefinger and with the aid of a wall-mounted mirror, or the like, guides the device to the ocular cul-de-sac defined by the lower eyelid. With the available free hand, the lower eyelid can be extended to more greatly expose the cul-de-sac for reception of the discharge end of the nozzle.

Thereafter, the user's thumb and forefinger compress the walls 22 to eject a drop of liquid having a volume that is predetermined by the diameter of the discharge passage 34 in the nozzle offset and the viscosity of the liquid being dispensed.

Due to the design of the dispenser and regulation of orifice size, it will be appreciated that the amount of pressure applied to the liquid by collapsing the side walls 22 of the chamber will be a relatively controlled pressure enabling the dispensation of a liquid drop of predetermined volume. The design is such, moreover, as to enable delivery of more viscous fluids such as, for example, that described in U.S. patent application Ser. No. 301,114, filed Jan. 25, 1989. In this way, therefore, the delivery of accurate dosage amounts of the dispensed substance is enhanced, particularly as compared with ointments, or the like.

In its preferred form the described apparatus is intended for unit-dose application. The simplicity of the design and the inexpensive form of fabrication of the device permit it to be simply disposed of following such single use. On the other hand, however, the invention, in its broadest scope, contemplates a device having a reservoir chamber 20 of sufficient capacity to contain an amount of liquid capable of permitting dispensation of a limited number, e.g., three to five additional doses. As indicated above, the design and organization of the device insures the reproducibility of accurate dosage dispensation.

It should be further understood that, although a preferred embodiment of the invention has been illustrated and described herein, changes and modifications can be made in the described arrangement without departing from the scope of the appended claims.

We claim:

1. A disposable liquid dispensing container suitable for self application of unit dose or limited multiple dose eye drops to the ocular cul-de-sac, comprising:

(a) an elongated hollow body having (1) a reservoir portion constituted by a chamber bounded by a pair of spaced, flat, generally parallel, compressible walls, said chamber being sized to contain a unit dose or limited multiple doses of eye drop liquid for expulsion upon compression of said walls by finger pinching;

(2) a generally cylindrical nozzle portion integral with said reservoir portion, the rear end of said nozzle portion extending from said chamber generally coplanar therewith and in an offset position adjacent one lateral side of said reservoir portion, said nozzle portion containing a passage connecting with said chamber, and the leading end of said nozzle portion being angularly offset with respect to the longitudinal extent of said chamber and with respect to the rear of said nozzle portion;

(b) a sealing closure integral with and terminating said leading end of said nozzle portion and separated therefrom by a line of weakness, the connection between said sealing closure and said nozzle portion being such that when the sealing closure is broken, the free end of said nozzle portion presents a discharge opening; and (c) a support tab integral with and extending between and connecting said closure and said nozzle portion to protect said nozzle portion against inadvertent disruption, said tab being a substantially flat body connected to said nozzle portion by spaced, frangible webs and being complementarily disposed in the space provided by the offset disposition of the rear of said nozzle portion.

2. A container according to claim 1 wherein said chamber is sized to contain up to about 0.5 ml of the liquid.

3. A container according to claim 1 wherein said angularly offset leading end of said nozzle portion is angularly offset out of the general plane of said reservoir portion and said rear end of said nozzle portion.

4. A container according to claim 1 wherein said compressible walls are roughened.

5. A container according to claim 1 wherein said sealing closure is a bulbous body separated from said leading end of said nozzle portion by a reduced neck defining said line of weakness, the connection being such that when the sealing closure is broken, the free end of said nozzle portion presents a spherical surface at said discharge opening.

6. A container according to claim 1 wherein said tab presents sufficient surface area for disposition of labelling.

7. A container according to claim 1 which is made of a low density plastic material.

8. A container according to claim 7 wherein the plastic material is polyethylene.

9. A container according to claim 7 wherein the plastic material is polypropylene.

10. A container according to claim 1 wherein the angular offset of the leading end of said nozzle portion is from about thirty to about sixty degrees.

11. A disposable liquid dispensing container suitable for self application of unit dose or limited mutliple dose eye drops to the ocular cul-de-sac, comprising:

(a) an elongated hollow body having
(1) a reservoir portion constituted by a chamber bounded by a pair of spaced, flat, generally parallel, compressible, roughened walls, said chamber having a hermetically sealed opening at its rear end for reception of liquid and being sized to contain a unit dose or limited multiple doses of eye drop liquid for expulsion upon compression of said walls by finger pinching;

(2) a generally cylindrical nozzle portion integral with said reservoir portion, the rear end of said nozzle portion extending from said chamber generally coplanar therewith and in an offset position adjacent one lateral side of said reservoir portion, said nozzle portion containing a passage connecting with said chamber, and the leading end of said nozzle portion being angularly offset with respect to the longitudinal extent of said chamber and with respect to the rear of said nozzle portion;

(b) a sealing closure integral with and terminating said leading end of said nozzle portion and separated therefrom by a line of weakness, the connection between said sealing closure and said nozzle portion being such that when the sealing closure is broken, the free end of said nozzle portion presents a discharge opening; and (c) a support tab integral with and extending between and connecting said closure and said nozzle portion to protect said nozzle portion against inadvertent disruption, said tab being a substantially flat body connected to said nozzle portion by spaced, frangible webs and being complementarily disposed in the space provided by the offset disposition of the rear of said nozzle portion.

12. A container according to claim 11 wherein said chamber is sized to contain up to about 0.5 mil of the liquid.

13. A container according to claim 11 wherein said angularly offset leading end of said nozzle portion is angularly offset out of the general plane of said reservoir portion and said rear end of said nozzle portion.

14. A container according to claim 11 wherein said sealing closure is a bulbous body separated from said leading end of said nozzle portion by a reduced neck defining said line of weakness, the connection being such that when the sealing closure is broken, the free end of said nozzle portion presents a spherical surface at said discharge opening.

15. A container according to claim 11 wherein said tab presents sufficient surface area for disposition of labelling.

16. A container according to claim 11 which is made of a low density plastic material.

17. A container according to claim 16 wherein the plastic material is polyethylene.

18. A container according to claim 16 wherein the plastic material is polypropylene.

19. A container according to claim 11 wherein the angular offset of the leading end of said nozzle portion is from about thirty to about sixty degrees.

20. A disposable liquid dispensing container suitable for self application of unit dose or limited multiple dose eye drops to the ocular cul-de-sac, comprising:

(a) an elongated hollow body having
(1) a reservoir portion constituted by a chamber bounded by a pair of spaced, flat, generally parallel, compressible, walls, said chamber having a hermetically sealed opening at its rear end for reception of liquid and being sized to contain a unit dose or limited multiple doses of eye drop liquid for expulsion upon compression of said walls by finger pinching;

(2) a generally cylindrical nozzle portion integral with said reservoir portion, the rear end of said nozzle portion extending from said chamber generally coplanar therewith and in an offset position adjacent one lateral side of said reservoir portion, said nozzle portion containing a passage connecting with said chamber, and the leading end of said nozzle portion being angularly offset with respect to the longitudinal extent of said chamber and with respect to the rear of said nozzle portion;

(b) a bulbous body sealing closure integral with and terminating said leading end of said nozzle portion and separated therefrom by a reduced neck defining a line of weakness, the connection between said bulbous body and said nozzle portion being such that when the sealing closure is broken, the free end of said nozzle portion presents a generally spherical surface; and (c) a support tab integral with and extending between and connecting said closure and said nozzle portion to protect said nozzle portion against inadvertent disruption, said tab being a substantially flat body connected to said nozzle portion by spaced, frangible webs and being complementarily disposed in the space provided by the offset disposition of the rear of said nozzle portion.

21. A container according to claim 20 wherein said chamber is sized to contain up to about 0.5 mil of the liquid.

22. A container according to claim 20 wherein said angularly offset leading end of said nozzle portion is angularly offset out of the general plane of said reservoir portion and said rear end of said nozzle portion.

23. A container according to claim 20 wherein said compressible walls are roughened.

24. A container according to claim 20 wherein said tab presents sufficient surface area for disposition of labelling.

25. A container according to claim 20 which is made of a low density plastic material.

26. A container according to claim 25 wherein the plastic material is polyethylene.

27. A container according to claim 25 wherein the plastic material is polypropylene.

28. A container according to claim 20 wherein the angular offset of the leading end of said nozzle portion is from about thirty to about sixty degrees.

29. A disposable liquid dispensing container suitable for self application of unit dose or limited multiple dose eye drops to the ocular cul-de-sac, comprising:

(a) an elongated hollow body having (1) a reservoir portion constituted by a chamber bounded by a pair of spaced, flat, generally parallel, compressible, roughened walls, said chamber having a hermetically sealed opening at its rear end for reception of liquid and being sized to contain a unit dose or limited multiple doses of eye drop liquid for expulsion upon compression of said walls by finger pinching;

(2) a generally cylindrical nozzle portion integral with said reservoir portion, the rear end of said nozzle portion extending from said chamber generally coplanar therewith and in an offset position adjacent one lateral side of said reservoir portion, said nozzle portion containing a passage connecting with said chamber, and the leading end of said nozzle portion being angularly offset with respect to the longitudinal extent of said chamber and with respect to the rear of said nozzle portion;

(b) a bulbous body sealing closure integral with and terminating said leading end of said nozzle portion and separated therefrom by a reduced neck defining a line of weakness, the connection between said bulbous body and said nozzle portion being such that when the sealing closure is broken, the free end of said nozzle portion presents a generally spherical surface; and (c) a support tab integral with and extending between and connecting said closure and said nozzle portion to protect said nozzle portion against inadvertent disruption, said tab being a substantially flat body connected to said nozzle portion by spaced, frangible webs and being complementarily disposed in the space provided by the offset disposition of the rear of said nozzle portion, said tab also preventing a labelling area.

30. A container according to claim 29 wherein said chamber is sized to contain up to about 0.5 mil of the liquid.

31. A container according to claim 29 wherein said angularly offset leading end of said nozzle portion is angularly offset out of the general plane of said reservoir portion and said rear end of said nozzle portion.

32. A container according to claim 29 which is made of a low density plastic material.

33. A container according to claim 32 wherein the plastic material is polyethylene.

34. A container according to claim 32 wherein the plastic material is polypropylene.

35. A container according to claim 32 wherein the angular offset of the leading end of said nozzle portion is from about thirty to about sixty degrees.

* * * * *